United States Patent
Kiuchi et al.

(10) Patent No.: US 7,067,030 B2
(45) Date of Patent: Jun. 27, 2006

(54) HEAT-PEELABLE ADHESIVE SHEET

(75) Inventors: Kazuyuki Kiuchi, Osaka (JP); Toshiyuki Oshima, Osaka (JP); Akihisa Murata, Osaka (JP); Yukio Arimitsu, Osaka (JP)

(73) Assignee: Nitto Denko Corporation, Osaka (JP)

( * ) Notice: Subject to any disclaimer, the term of this patent is extended or adjusted under 35 U.S.C. 154(b) by 102 days.

(21) Appl. No.: 10/400,792

(22) Filed: Mar. 28, 2003

(65) Prior Publication Data

US 2003/0203192 A1    Oct. 30, 2003

Related U.S. Application Data

(62) Division of application No. 09/806,093, filed as application No. PCT/JP99/05347 on Sep. 29, 1999, now abandoned.

(30) Foreign Application Priority Data

Sep. 30, 1998 (JP) ............................. P. 10-278952
Sep. 9, 1999 (JP) ............................. P. 11-255098

(51) Int. Cl.
*B32B 37/14* (2006.01)
*C09J 7/00* (2006.01)

(52) U.S. Cl. .................. 156/248; 156/83; 156/257; 156/268; 156/344; 521/56; 521/58; 521/60; 428/343; 428/354; 428/355 RA; 428/317.5

(58) Field of Classification Search ............. 156/83, 156/247, 248, 257, 268, 344; 521/56, 58, 521/60, 910; 428/343, 354, 355 RA, 317.5
See application file for complete search history.

(56) References Cited

U.S. PATENT DOCUMENTS

| 5,441,810 A | 8/1995 | Aizawa et al. |
| 5,609,954 A | 3/1997 | Aizawa et al. |

FOREIGN PATENT DOCUMENTS

| EP | 0 419 020 A1 | | 3/1991 |
| EP | 612823 A1 | | 8/1994 |
| JP | 56-61467 | * | 5/1981 |
| JP | 63-033487 | * | 2/1988 |
| JP | 63-186791 A | | 8/1988 |
| JP | 2-240182 | * | 9/1990 |
| JP | 02-305878 | * | 12/1990 |

(Continued)

OTHER PUBLICATIONS

European Search Report dated Mar. 25, 2002.

(Continued)

*Primary Examiner*—Linda Gray
(74) *Attorney, Agent, or Firm*—Sughrue Mion, PLLC

(57) ABSTRACT

A heat-peelable adhesive sheet which comprises a substrate and, formed on at least one side thereof, a heat-expandable layer containing heat-expandable microspheres and an adhesive layer comprising an adhesive substance and in which the substrate has heat resistance and stretchability can be used to cut an adherend so as to form and secure a sufficient space between the resultant cut pieces and can withstand a heat treatment for expanding the heat-expandable layer. Consequently, the adhesive sheet can heighten the operating efficiency and working efficiency in the step of separating and recovering the cut pieces.

6 Claims, 1 Drawing Sheet

FOREIGN PATENT DOCUMENTS

| | | | |
|---|---|---|---|
| JP | 05-043851 | * | 2/1993 |
| JP | 7-61458 A | | 3/1995 |
| JP | 7-145357 A | | 6/1995 |
| JP | 7-179828 A | | 7/1995 |
| JP | 07-183195 | * | 7/1995 |
| JP | 8-188756 A | | 7/1996 |
| JP | 10-168401 | * | 6/1998 |
| JP | 10-335836 A | | 12/1998 |

OTHER PUBLICATIONS

International Search Report dated Nov. 2, 1999.

* cited by examiner

HEAT-PEELABLE ADHESIVE SHEET

This is a divisional of Application No. 09/806,093 filed Mar. 27, 2001 now abandoned which is a 371 of PCT/JP99/05347, filed Sep. 29, 1999; the disclosure of which is incorporated herein by reference.

TECHNICAL FIELD

The present invention relates to a heat-peelable adhesive sheet which can be easily stripped from adherents by a heat treatment.

BACKGROUND ART

A heat-peelable adhesive sheet comprising a high-modulus film or sheet substrate made of a plastic or the like and formed thereon a pressure-sensitive adhesive layer containing a blowing agent is known as an adhesive sheet which is used in cutting a work to be cut, such as a semiconductor wafer or multilayer capacitor, into cut pieces of a given size in such a manner that the adhesive sheet is applied to the work to be cut and the cut pieces, e.g., chips, are easily separated and recovered therefrom (Examined Japanese Patent Publications Nos. 50-13878 and 51-24534, Unexamined Published Japanese Patent Applications Nos. 56-61468, 56-61469, and 60-252681, etc.). This heat-peelable adhesive sheet is intended to attain both the adhesive holding power which enables the adhesive sheet to withstand adherend cutting and the easy separation and recovery of cut pieces formed. Namely, this adhesive sheet has the following feature. The adhesive sheet has high tackiness when in contact with an adherend. However, at the time when cut pieces are to be recovered, the foamable pressure-sensitive adhesive layer is foamed or expanded by heating to thereby come to have a roughened surface. Due to the resultant decrease in the area in which the adhesive layer is adherent to the adherend, the tackiness is reduced or lost and, hence, the cut pieces can be easily separated.

However, in the case of the heat-peelable adhesive sheet described above, the cut pieces obtained by cutting an adherend are closely spaced. It is therefore difficult in, e.g., processes for producing electronic parts to use the adhesive sheet for cut-piece recovery techniques in which cut pieces should be located apart from each other, such as the picking-up recovery technique in which semiconductor chips are held by sides thereof in separating and recovering the same so as to prevent the surface ICs from being damaged and the multilayer capacitor chip recovery technique in which chips formed are prevented from adhering again to each other due to the binder used for the shape retention of a ceramic powder.

Consequently, an object of the invention is to provide a heat-peelable adhesive sheet which can be used to cut an adherend so as to form and secure a sufficient space between the resultant cut pieces and can withstand a heat treatment for expanding the heat-expandable layer.

Another object of the invention is to provide a heat-peelable adhesive sheet which can heighten the operating efficiency and working efficiency in the step of separating and recovering the cut pieces formed by cutting an adherend.

DISCLOSURE OF THE INVENTION

The present inventors made intensive studies in order to accomplish those objects. As a result, they have found that a heat-peelable adhesive sheet comprising a substrate having a heat-expandable layer formed on a surface thereof can be used to cut an adherend so as to form a sufficient space between the resultant cut pieces and does not deform through a heat treatment when the substrate is constituted of a film or sheet having specific properties. The invention has been thus completed.

Accordingly, the invention provides a heat-peelable adhesive sheet comprising a substrate and, formed on at least one side thereof, a heat-expandable layer containing heat-expandable microspheres and an adhesive layer comprising an adhesive substance, the substrate having heat resistance and stretchability.

In the figures, numeral 1 denotes a substrate, 2 a heat-expandable adhesive layer, 3 a separator, 4 an adhesive layer, 5 an adherend, 6 a cutting line, and 7 a cut piece.

BEST MODE FOR CARRYING OUT THE INVENTION

Figure 1:
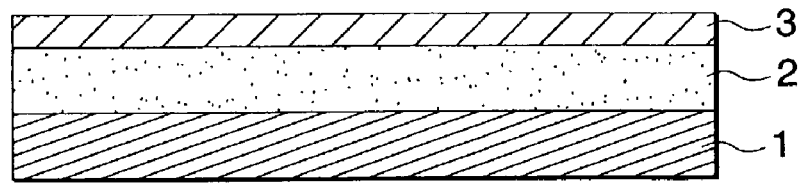
FIG. 1 is a diagrammatic sectional view illustrating one embodiment of the heat-peelable adhesive sheet of the invention.

Modes for carrying out the invention will be explained below in detail by reference to the drawings according to need. FIG. 1 is a diagrammatic sectional view illustrating one embodiment of the heat-peelable adhesive sheet of the invention.

In this embodiment, a heat-expandable adhesive layer 2 has been formed on one side of a substrate 1 and a separator 3 has been further superposed thereon.

The substrate 1 serves as a support for the heat-expandable adhesive layer 2, etc., and is made of a material having a stretching function and such a degree of heat resistance that the substrate is not impaired in mechanical strength by a heat treatment of the heat-expandable adhesive layer 2. Examples of such a material include a flexible vinyl chloride film or sheet containing a heat stabilizer, a stretchable polyester film or sheet, a flexible polyolefin film or sheet, a rubber type polymer sheet, a multilayered film or sheet comprising any of these substrate materials, and the like. The substrate 1 preferably has the property of being cut by a cutting means, such as a cutter, used for cutting an adherend.

Examples of the heat stabilizer in the heat stabilizer-containing flexible vinyl chloride film or sheet include metal soaps such as dibasic lead stearate, lead stearate, calcium stearate, barium stearate, zinc stearate, and magnesium stearate; organotin compounds such as dialkyltin dilaurates, dialkyltin maleates, and dialkyltin mercaptides; inorganic salts such as tribasic lead sulfate, lead oxide, dibasic lead phosphite, and lead orthosilicate; epoxy compounds such as epoxidized soybean oil; and the like. Preferred of these are metal soaps and organotin compounds.

These heat stabilizers can be used alone or in combination of two or more thereof. In the case of using a combination of two or more heat stabilizers, preferred examples thereof include a combination of a dialkyltin dilaurate and a dialkyltin maleate, a combination of zinc stearate and barium stearate, a combination of calcium stearate and zinc stearate optionally with epoxidized soybean oil, and the like.

The addition amount of the heat stabilizer is, for example, from 0.5 to 10 parts by weight, preferably about from 1 to 5 parts by weight, per 100 parts by weight of the vinyl chloride resin. Besides the heat stabilizer, a chelator such as a phosphorous acid ester (triphenyl phosphite, etc.) or another chelator is preferably added to the flexible vinyl chloride film or sheet. The addition amount of the chelator is, for example, from 0.1 to 3 parts by weight, preferably about from 0.3 to 1.5 parts by weight, per 100 parts by weight of the vinyl chloride resin. The flexible vinyl chloride film or sheet may contain other stabilizers such as, for example, antioxidants, e.g., alkylphenols (2,6-di-t-butyl-p-cresol, etc.), ultraviolet absorbers, e.g., benzotriazole [2-(2'-hydroxy-5-methylphenyl)benzotriazole, etc.], and the like.

Besides homopolymers of vinyl chloride, examples of the resin constituting the flexible vinyl chloride film or sheet containing a heat stabilizer include vinyl chloride copolymers such as vinyl chloride/vinyl acetate copolymers, vinyl chloride/ethylene copolymers, vinyl chloride/propylene copolymers, vinyl chloride/acrylic ester copolymers, vinyl chloride/vinylidene chloride copolymers, vinyl chloride/acrylonitrile copolymers, vinyl chloride/maleic ester copolymers, EVA (ethylene/vinyl acetate copolymer)/vinyl chloride graft copolymers, and polyurethane/vinyl chloride graft copolymers. In case where a non-heat-resistant flexible vinyl chloride film or sheet containing no heat stabilizers is used as a substrate, the substrate deforms upon heat treatment of the adhesive sheet, whereby the surface smoothness of the adhesive sheet itself is impaired, leading to considerably reduced working efficiency in cut piece recovery, etc.

Examples of the stretchable polyester film or sheet include films or sheets made of a blend of a saturated polyester (e.g., poly(ethylene terephthalate), poly(butylene terephthalate), or the like) with a modified polyolefin (e.g., an acid-modified polyolefin such as acrylic-acid-modified polyethylene or acrylic-acid-modified polypropylene, an epoxy-modified polyolefin, or the like) or with a rubber type polymer (e.g., a thermoplastic elastomer such as an ethylene/propylene rubber, a polyester elastomer, or an ethylene/acrylic rubber or the like) or the like or made of poly(ethylene naphthalate) or the like. In case of using as a substrate an ordinary poly(ethylene terephthalate) film or the like which is not stretchable, it is difficult to form and secure a sufficient space between the cut pieces obtained by cutting an adherend.

Examples of the flexible polyolefin film or sheet include films or sheets made of a resin having hard segments consisting of polypropylene or the like and soft segments consisting of an ethylene/propylene copolymer or the like, films or sheets made of flexible polyethylene, and the like.

Examples of the rubber type polymer constituting the rubber type polymer sheet include natural rubber, isoprene rubber, butadiene rubber, 1,2-polybutadiene, chloroprene rubber, styrene/butadiene rubber, nitrile rubber, butyl rubber, ethylene/propylene rubber, acrylic rubbers, epichlorohydrin rubbers, silicone rubbers, fluororubbers, urethane rubbers, chlorosulfonated polyethylene, polysulfide rubbers, chlorinated polyethylene, thermoplastic elastomers (e.g., styrene-based, polyurethane type, polyester type, fluoropolymer type, and polyamide type thermoplastic elastomers and the like), and the like. Frequently used among these are, for example, acrylic rubbers such as alkyl acrylate/2-chloroethyl vinyl ether copolymers, alkyl acrylate/acrylonitrile copolymers, ethylene/vinyl acetate/acrylic ester copolymer elastomers, and ethylene/acrylic ester copolymers; silicone rubbers such as dimethylsiloxane-based, methylvinylsiloxane-based, methylphenylvinylsiloxane-based, and methylfluoroalkyl-containing silicone rubbers; fluororubbers such as hexafluoropropene/vinylidene fluoride copolymers, hexafluoropropene/vinylidene fluoride/tetrafluoroethylene copolymers, tetrafluoroethylene/propylene copolymers, and tetrafluoroethylene/perfluoro(methyl vinyl ether) copolymers; and the like. The polymer constituting the substrate 1 may have a crosslinked structure.

The substrate 1 may be a single-layer structure made of a substrate material described above or may be a multilayer structure comprising a suitable combination of substrate materials described above. Use of a multilayer structure comprising a combination of suitable substrate materials makes it possible to attain impartation of mechanical rigidity to the substrate, improvement of the heat resistance of the substrate, improvement of adhesion to the heat-expandable adhesive layer 2 and to the adhesive layer 4 which will be described later, improvement of working efficiency in the step of adherend cutting, etc.

The tensile elongation at break [in accordance with JIS K 7113 (sheet) or JIS K 7127 (film)] of the film or sheet constituting the substrate 1 is usually about 10% or higher, preferably about 250% or higher, from the standpoint of widening the space between the cut pieces resulting from adherend cutting. Although the upper limit of the elongation at break is not particularly limited, it is preferably 1,000%, more preferably about 800%, so as to prevent the substrate from sagging due to the weight of the adherend.

The thickness of the substrate 1 can be suitably selected in such a range as not to impair operating efficiency and working efficiency in the steps of application to an adherend, cutting of the adherend, separation and recovery of cut pieces, etc. In general, however, it is about from 10 µm to 10 mm. The surfaces of the substrate 1 may have undergone an ordinary surface treatment, e.g., a chemical or physical treatment such as treatment with chromic acid, exposure to ozone, exposure to flame, exposure to high-voltage electric shock, treatment with ionizing radiation, etc., a coating treatment with a primer (e.g., the adhesive substance which will be described later), or the like for the purpose of enhancing adhesion to the adjacent layer, holding power, etc.

The heat-expandable adhesive layer 2 comprises an adhesive substance for imparting tackiness and heat-expandable microspheres for imparting thermal expansibility. Although the single layer (heat-expandable adhesive layer 2) in the embodiment shown in FIG. 1 combines two functions, i.e., tackiness and heat expansibility, these two functions may be separately allotted in the invention to form an adhesive layer having tackiness and a heat-expandable layer having thermal expansibility. For example, a heat-expandable layer containing heat-expandable microspheres and an adhesive layer comprising an adhesive substance may be formed in this order on at least one side of a substrate. In this description, in explaining the heat-expandable adhesive layer, this layer is included in each of a heat-expandable layer and an adhesive layer unless otherwise indicated.

As the adhesive substance can be used an ordinary adhesive. In general, however, a heat-activable adhesive, an adhesive activable with water or an organic solvent, a pressure-sensitive adhesive, or the like is used.

Examples of the heat-activable adhesive include hot-melt adhesives, thermally pressure-sensitive adhesives which contain a low-melting heat-meltable resin and which have low tackiness at ordinary temperature but come to have high tackiness upon heating (see, for example, Unexamined Published Japanese Patent Application No. 56-13040, Examined Japanese Patent Publication No. 2-50146, etc.), and the like.

Examples of the pressure-sensitive adhesive include rubber-based pressure-sensitive adhesives, acrylic pressure-sensitive adhesives, styrene/conjugated diene block copolymer type pressure-sensitive adhesives, silicone-based pressure-sensitive adhesives, ultraviolet-curable pressure-sensitive adhesives, pressure-sensitive adhesives with improved creep characteristics which contain a heat-meltable resin having a low melting point (especially 200° C. or lower), and the like (see, for example, Unexamined Published Japanese Patent Applications Nos. 56-61468, 61-174857, 63-17981, and 56-13040, etc.).

Examples of the rubber-based pressure-sensitive adhesives include pressure-sensitive adhesives containing natural rubber or various synthetic rubbers as the base polymer, pressure-sensitive adhesives containing as the base polymer a silicone rubber represented by dimethylpolysiloxane, and the like.

Examples of the acrylic pressure-sensitive adhesives include pressure-sensitive adhesives containing as the base polymer an acrylic polymer (homopolymer or copolymer) produced using one or more monomer ingredients selected from alkyl (meth)acrylates (such as the esters with $C_{1-20}$ alkyls, such as, e.g., the methyl ester, ethyl ester, propyl ester, isopropyl ester, butyl ester, isobutyl ester, s-butyl ester, t-butyl ester, pentyl ester, hexyl ester, heptyl ester, octyl ester, 2-ethylhexyl ester, isooctyl ester, isodecyl ester, dodecyl ester, tridecyl ester, pentadecyl ester, hexadecyl ester, heptadecyl ester, octadecyl ester, nonadecyl ester, and eicosyl ester) and cycloalkyl (meth)acrylates (such as the esters with $C_{3-20}$ cycloalkyls, such as, e.g., the cyclopentyl ester and cyclohexyl ester), and the like.

As an acrylic pressure-sensitive adhesive can also be used a pressure-sensitive adhesive containing as the base polymer a copolymer of one or more of those alkyl (or cycloalkyl) (meth)acrylates with one or more other monomers used for modifying adhesive properties or for another purpose. Examples of such other monomers include carboxyl-containing monomers such as acrylic acid, methacrylic acid, carboxyethyl acrylate, carboxypentyl acrylate, itaconic acid, maleic acid, fumaric acid, and crotonic acid; acid anhydride monomers such as maleic anhydride and itaconic anhydride; hydroxyl-containing monomers such as 2-hydroxyethyl (meth)acrylate, 2-hydroxypropyl (meth)acrylate, and 4-hydroxybutyl (meth)acrylate; sulfo-containing monomers such as styrenesulfonic acid, allylsulfonic acid, 2-(meth)acrylamido-2-methylpropanesulfonic acid, and (meth)acrylamidopropanesulfonic acid; phosphate-containing monomers such as 2-hydroxyethyl acryloylphosphate; (N-substituted) amide monomers such as (meth)acrylamide, N-butyl(meth)acrylamide, N-methylol(meth)acrylamide, and N-methylolpropane(meth)acrylamide; alkylaminoalkyl (meth)acrylate monomers such as aminoethyl (meth)acrylate and N,N-dimethylaminoethyl (meth)acrylate; alkoxyalkyl (meth)acrylate monomers such as methoxyethyl (meth)acrylate and ethoxyethyl (meth)acrylate; maleimide monomers such as N-cyclohexylmaleimide and N-isopropylmaleimide; itaconimide monomers such as N-methylitaconimide and N-ethylitaconimide; succinimide monomers such as N-(meth)acryloyloxymethylenesuccinimide and N-(meth)acryloyl-6-oxyhexamethylenesuccinimide; vinyl monomers such as vinyl acetate, vinyl propionate, N-vinylpyrrolidone, methylvinylpyrrolidone, styrene, and α-methylstyrene; cyanoacrylate monomers such as acrylonitrile and methacrylonitrile; epoxy-containing acrylic monomers such as glycidyl (meth)acrylate; acrylic glycol ester monomers such as polyethylene glycol (meth)acrylate and polypropylene glycol (meth)acrylate; acrylic ester monomers having one or more heterocycles, halogen atoms, silicon atoms, or the like, such as tetrahydrofurfuryl (meth)acrylate, fluoro(meth)acrylates, and silicone (meth)acrylates; polyfunctional monomers such as hexanediol di(meth)acrylate, (poly)ethylene glycol di (meth) acrylate, (poly) propylene glycol di (meth) acrylate, neopentyl glycol di(meth)acrylate, pentaerythritol di(meth)acrylate, trimethylolpropane tri(meth)acrylate, pentaerythritol tri(meth)acrylate, dipentaerythritol hexa(meth)acrylate, epoxy acrylates, polyester acrylates, and urethane acrylates; olefin monomers such as isoprene, butadiene, and isobutylene; vinyl ether monomers such as vinyl ether; and the like. These monomers can be used alone or two or more thereof can be used.

Preferred among the adhesive substances described above are the pressure-sensitive adhesives from the standpoint of ease of application to an adherend. In the case where an adhesive substance and heat-expandable microspheres are contained in the same layer as in the embodiment described above, it is desirable to select and use an adhesive substance which imposes a minimum of restriction on the foaming or expansion of the heat-expandable microspheres during heating. The adhesive substances shown above can be used alone or in combination of two or more thereof.

Besides the adhesive substances, appropriate additives may be incorporated into the adhesive layer, such as a crosslinking agent (e.g., an isocyanate crosslinking agent, epoxy crosslinking agent, etc.), a tackifier (e.g., a rosin derivative resin, polyterpene resin, petroleum resin, oil-soluble phenolic resin, etc.), a plasticizer, a filler, and an antioxidant.

The heat-expandable microspheres may be microspheres formed by surrounding a substance which readily becomes gaseous and expands upon heating, such as, e.g., isobutane, propane, or pentane, in elastic shells. The shells are usually made of a thermoplastic substance, a heat-meltable substance, a substance which bursts due to thermal expansion, or the like. Examples of such substances constituting the shells include vinylidene chloride/acrylonitrile copolymers, poly(vinyl alcohol), poly(vinyl butyral), poly(methyl methacrylate), polyacrylonitrile, poly(vinylidene chloride), polysulfones, and the like. The heat-expandable microspheres can be produced by an ordinary method such as, e.g., the coacervation method or the interfacial polymerization method. As the heat-expandable microspheres can also be used a commercial product such as Microsphere [trade name; manufactured by Matsumoto Yushi-Seiyaku Co., Ltd.].

The average particle diameter of the heat-expandable microspheres is preferably about, for example, from 1 to 50 μm from the standpoints of dispersibility, suitability for thin-film formation, etc. Furthermore, in order for the heat-expandable microspheres to efficiently reduce the tackiness of the adhesive layer containing an adhesive substance through a heat treatment, the microspheres preferably have such a moderate strength that they do not burst until their degree of volume expansion reaches 5 times or more, especially 10 times or more. In case of using heat-expandable microspheres which burst at a low degree of expansion or using a heat-expanding agent which has not been microencapsulated, the area in which the adhesive layer is adherent to an adherend cannot be sufficiently reduced and satisfactory separability is difficult to obtain.

The amount of the heat-expandable microspheres to be used varies depending on the kind thereof. However, the amount thereof is, for example, from 10 to 200 parts by weight, preferably from 25 to 125 parts by weight, per 100 parts by weight of the base polymer constituting the heat-expandable adhesive layer 2. In the case where a heat-expandable layer and an adhesive layer are formed as separate layers, the use amount of the heat-expandable microspheres is, for example, from 10 to 98% by weight, preferably about from 15 to 95% by weight, based on the whole heat-expandable layer.

The heat-expandable adhesive layer 2 can be formed by an ordinary method such as, for example, a method in which a coating fluid comprising an adhesive substance and heat-expandable microspheres and optionally containing a solvent is applied to a substrate 1 or a method in which the coating fluid is applied to an appropriate separator (release paper or the like) to form a heat-expandable adhesive layer and this layer is transferred to a substrate 1.

In the case where a heat-expandable layer and an adhesive layer are formed as separate layers, the heat-expandable layer can be formed, for example, by applying a coating fluid comprising heat-expandable microspheres and a binder to a substrate 1. As the binder can be used a rubber type, resin type, or another polymeric compound which allows the heat-expandable microspheres to foam or expand. The adhesive layer can be formed from a coating fluid comprising an adhesive substance by the same method as for the heat-expandable adhesive layer 2 described above.

The thickness of the heat-expandable adhesive layer 2 is, for example, 300 μm or smaller (about from 5 to 300 μm), preferably about from 10 to 150 μm, from the standpoint of preventing the adhesive layer from leaving on the adherend an adhesive residue resulting from cohesive failure after the foaming or expansion of the heat-expandable microspheres. In the case where a heat-expandable layer and an adhesive layer are formed as separate layers, the thickness of the heat-expandable layer is, for example, from 3 to 300 μm, preferably about from 5 to 150 μm, and the thickness of the adhesive layer is, for example, from 0.1 to 100 μm, preferably about from 0.5 to 30 μm.

As the separator 3 can, for example, be used a substrate surface-coated with a release agent represented by a silicone resin, a long-chain-alkyl acrylate resin, a fluororesin, or the like, a lowly tacky substrate made of a non-polar polymer such as polyethylene or polypropylene, or the like. The separator 3 may be used as a provisional support in transferring the heat-expandable adhesive layer 2 or the like to the substrate 1 as described above, or may be used as a protective material for protecting the heat-expandable adhesive layer 2 or the like until the adhesive sheet is subjected to practical use. The separator 3 need not be always disposed.

Incidentally, the heat-expandable adhesive layer 2 (or the heat-expandable layer and the adhesive layer) can be formed not only on one side of the substrate 1 but on each side thereof. It is also possible to form the heat-expandable adhesive layer 2 on one side of the substrate 1 and further form, on the other side thereof, an ordinary adhesive layer not containing heat-expandable microspheres. Furthermore, an interlayer may be formed, for example, between the substrate 1 and the heat-expandable adhesive layer 2.

Figure 2:
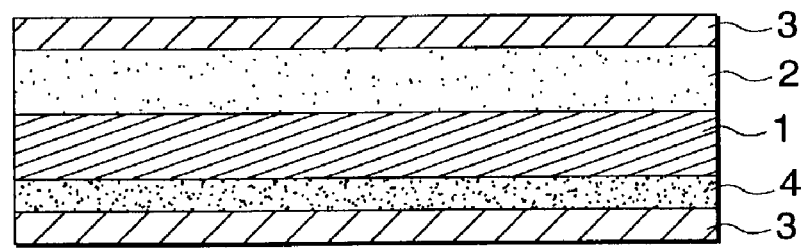
FIG. 2 is a diagrammatic sectional view illustrating another embodiment of the heat-peelable adhesive sheet of the invention.

FIG. 2 is a diagrammatic sectional view illustrating another embodiment of the heat-peelable adhesive sheet of the invention. In this embodiment, a heat-expandable adhesive layer 2 has been formed on one side of a substrate 1 and a separator 3 has been superposed thereon. Furthermore, an adhesive layer 4 and a separator 3 have been superposed on the other side of the substrate 1. This adhesive sheet differs from the adhesive sheet of FIG. 1 only in that the adhesive layer 4 and a separator 3 have been disposed on that side of the substrate 1 which is opposite to the side where the heat-expandable adhesive layer 2 has been formed.

The adhesive layer 4 comprises an adhesive substance. As this adhesive substance can be used the same adhesive substance as in the heat-expandable adhesive layer 2 described above. The thickness of the adhesive layer 4 can be selected in such a range as not to impair operating efficiency and the like in application to an adherend, cutting of the adherend, separation and recovery of cut pieces, etc. In general, however, it is about from 5 to 50 μm. The adhesive layer 4 can be formed by the same method as for the heat-expandable adhesive layer 2 described above. As each separator 3 can be used the same one as the separator 3 disposed on the heat-expandable adhesive layer 2 described above. Such an adhesive sheet can be used in the state of being fixed to the surface of a pedestal by utilizing the adhesive layer 4.

Figure 3:
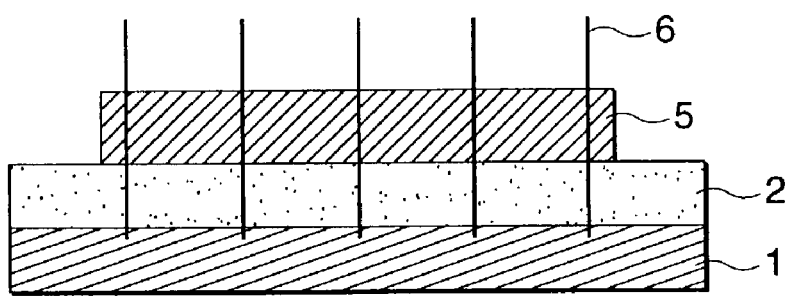
FIGS. 3 and 4 are views illustrating the heat-peelable adhesive sheet of FIG. 1 which is being used.
Figure 4:
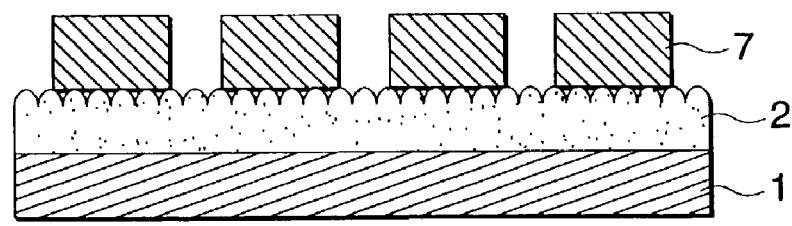

FIGS. 3 and 4 are views illustrating the heat-peelable adhesive sheet of FIG. 1 which is being used. More particularly, FIG. 3 is a diagrammatic sectional view illustrating the state of the heat-peelable adhesive sheet of FIG. 1 having an adherend which is adhesively held thereon and has been cut into a given size. FIG. 4 is a diagrammatic sectional view illustrating the heat-peelable adhesive sheet which was in the state shown in FIG. 3 and has undergone a heat treatment and a stretching treatment.

In FIG. 3, numeral 5 denotes an adherend (work to be cut) and 6 denotes a cutting line for the adherend 5. In FIG. 4, numeral 7 denotes a cut piece formed by cutting the adherend 5.

Application of the adhesive layer (heat-expandable adhesive layer 2) of the heat-peelable adhesive sheet to the adherend 5 can be accomplished by using an appropriate pressing means, e.g., a rubber roller, laminating roll, pressing apparatus, or the like, to conduct a press-bonding treatment or by another method. In the application treatment, the adhesive substance may be activated if desired by heating at a temperature in a range where the heat-expandable microspheres do not expand or by applying water or an organic solvent, according to the type of the adhesive substance.

The cutting of the adherend 5 can be conducted by an ordinary cutting means. Conditions for the heat treatment can be suitably fixed according to the surface state and heat resistance of the adherend 5 (or cut pieces 7), kind of the heat-expandable microspheres, heat resistance of the adhesive sheet, etc. However, general conditions include a temperature of 350° C. or lower and a treatment time of 5 minutes or shorter, and especially preferably include a temperature of from 100 to 200° C. and a treatment time of about from 1 to 90 seconds. The heat treatment can be conducted at a suitable stage according to the intended use of the adhesive sheet. Methods for heating include hot-air heating, contact with a hot plate, infrared heating, and the like. However, any heating method may be used without particular limitations as long as it evenly foams or expands the heat-expandable layer and neither fouls nor damages the adherend.

The stretching treatment of the adhesive sheet can be conducted, for example, by using a stretching means ordinarily used for two-dimensionally stretching sheets.

Since the heat-peelable adhesive sheet of the invention has an adhesive layer comprising an adhesive substance, the adherend 5 can be cut into a given size without sliding on or separating from the adhesive sheet during the cutting. Furthermore, since the adhesive sheet has a heat-expandable layer containing heat-expandable microspheres, the heat-expandable microspheres are promptly foamed or expanded by a heat treatment and the heat-expandable layer changes in volume to form a three-dimensional structure with a rough surface. Consequently, the area in which the adhesive layer is adherent to the cut pieces 7 resulting from the cutting decreases considerably, and the adhesive strength hence decreases greatly. In this heat treatment, the substrate 1 does not deform because it has heat resistance, whereby the surface smoothness of the adhesive sheet can be maintained. In addition, since the substrate 1 in the heat-peelable adhesive sheet of the invention has stretchability, the space between the cut pieces 7 can be easily enlarged to a desired degree by stretching the adhesive sheet in an in-plane direction. Thus, a considerable decrease in adhesive strength is attained by the heat treatment and an increase in the space between the cut pieces is attained by the stretching treatment. As a result, the operating efficiency and working efficiency in the step of separating and recovering the cut pieces 7 are greatly improved and the production efficiency also can be greatly improved.

Although the heat-peelable adhesive sheet of the invention may be used in applications in which an adherend is permanently bonded, it is suitable for use in applications in which an adherend is bonded for a given period and, after accomplishment of the purpose of bonding, the bonded state is required or desired to be ended. Besides semiconductor wafer fixing materials, examples of such applications include carrier tapes, temporarily fixing materials, or fixing materials for, e.g., conveying or temporarily fixing parts in steps for assembling various electrical apparatus, electronic apparatus, displays, and the like and surface protective materials, masking materials, or the like used for preventing metal plates, plastic plates, glass plates, or the like from being fouled or damaged. The adhesive sheet is especially suitable for use in processes for producing electronic parts in the case of employing the picking-up recovery technique in which cut pieces such as semiconductor chips are held by sides thereof in separating and recovering the same, and for use in the recovery of multilayer capacitor chips and in similar applications.

The invention will be explained below in more detail based on Examples, but the invention should not be construed as being limited by these Examples in any way. Hereinafter, "parts" means "parts by weight".

EXAMPLE 1

Ten parts of a rosin phenol tackifier and 2 parts of an isocyanate crosslinking agent were incorporated into a toluene solution containing 100 parts of an acrylic copolymer formed from 40 parts of 2-ethylhexyl acrylate, 60 parts of ethyl acrylate, and 3 parts of hydroxyethyl acrylate. Thus, a toluene solution of an acrylic pressure-sensitive adhesive was obtained. Subsequently, 25 parts of heat-expandable microspheres (trade name, Matsumoto Microsphere F-30; manufactured by Matsumoto Yushi-Seiyaku Co., Ltd.) were added to the solution to prepare a coating fluid.

A resin having 50 parts of hard segments consisting of polypropylene and 50 parts of soft segments consisting of an ethylene/propylene copolymer (trade name, KS-221P; manufactured by Montell Polyolefins Company; MFR, 2.5; density, 0.89 g/cm$^3$) was extrusion-molded to produce a polyolefin film having a thickness of 75 μm. One side of this film was subjected to a corona treatment.

A polyester film having a silicone-treated surface was coated with the coating fluid and the coating was dried to form a heat-expandable adhesive layer having a thickness of 40 μm. This heat-expandable adhesive layer was transferred to the corona-treated surface of the polyolefin film to obtain a heat-peelable adhesive sheet.

EXAMPLE 2

Into a toluene solution of 100 parts of a silicone rubber adhesive was incorporated 0.9 parts of a silicone-curing agent to obtain a toluene solution of a silicone-based pressure-sensitive adhesive. Subsequently, 30 parts of heat-expandable microspheres (trade name, Matsumoto Microsphere F-50; manufactured by Matsumoto Yushi-Seiyaku Co., Ltd.) were added to the solution to prepare a coating fluid.

A silicone rubber compound (trade name, KE931-U; manufactured by Shin-Etsu Chemical Co., Ltd.) was extrusion-molded to obtain a silicon rubber sheet having a thickness of 2 mm.

This silicone rubber sheet was coated with the coating fluid and the coating was dried to obtain a heat-peelable adhesive sheet having a heat-expandable adhesive layer having a thickness of 45 μm.

EXAMPLE 3

Ten parts of a terpene phenol tackifier and 2.5 parts of an isocyanate crosslinking agent were incorporated into a toluene solution containing 100 parts of an acrylic copolymer formed from 75 parts of 2-ethylhexyl acrylate, 25 parts of ethyl acrylate, 3 parts of methyl methacrylate, and 5 parts of hydroxyethyl acrylate. Thus, a toluene solution of an acrylic pressure-sensitive adhesive was obtained. Subsequently, 30 parts of heat-expandable microspheres (trade name, Matsumoto Microsphere F-30; manufactured by Matsumoto Yushi-Seiyaku Co., Ltd.) were added to the solution to prepare a coating fluid.

A flexible polyolefin resin (trade name, CAP350; manufactured by Ube Industries, Ltd.) was subjected as an interlayer material to coextrusion molding together with polyethylene to obtain a three-layer film having a layer constitution of polyethylene/flexible polyolefin resin (CAP350)/polyethylene and having a total thickness of 100 μm.

A polyester film having a silicone-treated surface was coated with the coating fluid and the coating was dried to form a heat-expandable adhesive layer having a thickness of 35 μm. This heat-expandable adhesive layer was transferred to a surface of the three-layer film to obtain a heat-peelable adhesive sheet.

COMPARATIVE EXAMPLE 1

The same procedure as in Example 1 was conducted, except that a flexible poly (vinyl chloride) having a thickness of 25 μm (trade name, KM Film; manufactured by Mitsubishi Kasei Vinyl) was used as a substrate in place of the polyolefin film. Thus, a heat-peelable adhesive sheet was obtained.

COMPARATIVE EXAMPLE 2

The same procedure as in Example 2 was conducted, except that a polyester film having a thickness of 75 μm (trade name, Lumirror S-10; manufactured by Toray Industries, Inc.) was used as a substrate in place of the silicone rubber sheet. Thus, a heat-peelable adhesive sheet was obtained.

Evaluation Tests

The adhesive sheets (20-mm wide) obtained in the Examples and Comparative Examples each was applied, on the heat-expandable adhesive layer side, to a polyester tape having a thickness of 25 μm (Lumirror S-10, manufactured by Toray Industries, Inc.), and the 180° peel adhesive strength (tackiness) thereof (N/20 mm) (peel rate, 300 mm/min; 23° C.) was measured before and after heating. Furthermore, each adhesive sheet applied to a dicing ring was attached to a die bonder (CSP-100, NEC Machinery Corporation) and pulled down over 10 mm to examine the substrate for stretchability before and after heating. Each adhesive sheet which had undergone the heating was also examined visually for substrate deformation.

Incidentally, the heat treatment of the adhesive sheets of Example 2 and Comparative Example 2 was conducted on a 130° C. hot plate for 60 seconds, and that of the adhesive sheets of Examples 1 and 3 and Comparative Example 1 was conducted on a 100° C. hot plate for 60 seconds. The results are shown in Table 1.

TABLE 1

|  | Stretchable or non-stretchable | Substrate deformation through heating | Tackiness (N/20 mm) Before heating | Tackiness (N/20 mm) After heating |
|---|---|---|---|---|
| Example 1 | Stretchable | Not deformed | 3.5 | 0.03 |
| Example 2 | Stretchable | Not deformed | 4.4 | 0.00 |
| Example 3 | Stretchable | Not deformed | 3.2 | 0.02 |
| Comparative Example 1 | Stretchable | Deformed | 3.8 | 0.00 |
| Comparative Example 2 | Non-stretchable | Not deformed | 4.2 | 0.10 |

The adhesive sheets themselves of Examples 1, 2, and 3 showed stretchability regardless of whether or not they had undergone a heat treatment. In contrast, in the adhesive sheet of Comparative Example 1, the substrate film was softened by the heat treatment and the surface smoothness of the adhesive sheet itself was lost. Furthermore, stretchability was not observed in the adhesive sheet of Comparative Example 2. In each of the Examples and Comparative Examples, no adhesive residue was observed on the polyester tape after the measurement of tackiness.

INDUSTRIAL APPLICABILITY

The heat-peelable adhesive sheet of the invention can be used to cut an adherend so as to form and secure a sufficient space between the resultant cut pieces and can withstand a heat treatment for expanding the heat-expandable layer. Consequently, the adhesive sheet can heighten the operating efficiency and working efficiency in the step of separating and recovering the cut pieces formed by cutting the adherend and, hence, can greatly improve the efficiency of production of cut pieces such as semiconductor chips.

The invention claimed is:

1. A method of separating and recovering cut workpieces of a semiconductor wafer or multilayer capacitor, comprising applying a heat-peelable adhesive sheet to the semiconductor wafer or multilayer capacitor to be cut into workpieces thereof, cutting the semiconductor wafer or multilayer capacitor into workpieces, heating and stretching theat-peelable adhesive sheet to separate the workpieces, and recovering the cut workpieces, wherein the heat-peelable adhesive sheet consists essentially of a substrate and, formed on at least one side thereof, a heat-expandable layer containing heat-expandable microspheres and an adhesive layer comprising an adhesive substance, the heat-expandable layer being located between the substrate of the heat-peelable adhesive sheet and the adhesive layer and said substrate having heat resistance, stretchability and a tensile elongation at break of about 250% or higher.

2. The method as claimed in claim 1, wherein the substrate of the heat-peelable adhesive sheet comprises a substrate material selected from the group consisting of a flexible vinyl chloride film containing a heat stabilizer, a stretchable polyester film, a rubber polymer film, and a multilayered film comprising any of said substrate materials.

3. The method as claimed in claim 1, wherein the substrate has the heat-expandable layer and the adhesive layer in this order on one side thereof, and further has an adhesive layer comprising an adhesive substance on the other side thereof.

4. A method of separating and recovering cut workpieces, comprising applying a heat-peelable adhesive sheet to an adherend to be cut into workpieces, cutting the adherend into workpieces, heating and stretching theat-peelable adhesive sheet to separte the workpieces, and recovering the cut workpieces, wherein the heat-peelable adhesive sheet consists essentially of a substrate and, formed on at least one side thereof, a heat-expandable layer containing heat-expandable microspheres and an adhesive layer comprising an adhesive substance, wherein the heat-expandable layer and the adhesive layer are formed as single layer, said substrate of the heat-peelable adhesive sheet having heat resistance, stretchability and a tensile elongation at break of about 250% or higher.

5. The method as claimed in claim 4, wherein the substrate of the heat-peelable adhesive sheet comprises a substrate material selected from the group consisting of a flexible vinyl chloride film containing a heat stabilizer, a stretchable polyester film, a rubber polymer film, and a multilayered film comprising any of said substrate materials.

6. The method as claimed in claim 4, wherein the substrate has the heat-expandable layer and the adhesive layer formed as a single layer on one side thereof, and further has an adhesive layer comprising an adhesive substance on the other side thereof.

* * * * *